(12) United States Patent
Armencha et al.

(10) Patent No.: US 8,222,610 B2
(45) Date of Patent: Jul. 17, 2012

(54) AUXILIARY COMPONENT FOR MEDICAL DEVICE HAVING ADDITIONAL FUNCTIONALITY

(75) Inventors: Valeriy Armencha, Long Island City, NY (US); Mark Abramovich, Long Island City, NY (US)

(73) Assignee: Sirona Dental Systems GmbH, Bensheim (DE)

( * ) Notice: Subject to any disclaimer, the term of this patent is extended or adjusted under 35 U.S.C. 154(b) by 320 days.

(21) Appl. No.: 12/552,348

(22) Filed: Sep. 2, 2009

(65) Prior Publication Data

US 2011/0051903 A1    Mar. 3, 2011

(51) Int. Cl.
*A61B 6/14* (2006.01)
(52) U.S. Cl. .................... 250/370.09; 378/191
(58) Field of Classification Search .......... 378/191; 439/162, 577, 604, 909; 600/394; D24/161; 250/370.09
See application file for complete search history.

(56) References Cited

U.S. PATENT DOCUMENTS

| | | |
|---|---|---|
| 4,341,992 A | 7/1982 | Goldstein |
| 5,677,537 A | 10/1997 | Pfeiffer ................ 250/370.09 |
| 6,030,119 A | 2/2000 | Tachibana et al. |
| 6,350,232 B1 | 2/2002 | Hascoet et al. ............ 600/124 |
| 6,549,794 B1 | 4/2003 | Nadeau, Jr. et al. ......... 600/310 |
| 6,811,312 B2 | 11/2004 | Bratslavsky et al. |
| 6,924,486 B2 | 8/2005 | Schick et al. |
| 7,193,219 B2 | 3/2007 | Schick et al. |
| 2002/0166946 A1 | 11/2002 | Iizuka et al. ............. 250/201.2 |
| 2004/0210259 A1 | 10/2004 | Rock et al. |
| 2005/0255424 A1 | 11/2005 | Hack et al. |
| 2007/0198073 A1 | 8/2007 | MacDonald et al. ........ 607/122 |
| 2009/0014661 A1* | 1/2009 | Yagi et al. .............. 250/370.11 |

OTHER PUBLICATIONS

International Search Report issued in the corresponding International Application No. PCT/US2010/047640—2 pages, Oct. 2010.

* cited by examiner

*Primary Examiner* — Constantine Hannaher
(74) *Attorney, Agent, or Firm* — Fitzpatrick, Cella, Harper & Scinto

(57) ABSTRACT

An auxiliary component that is used with a medical device is modified to provide for additional or enhanced functionality. In one specific embodiment, a sheath surrounds an intraoral electronic image sensor, and is provided with signal conductors integrated therein. Electrical communication is provided between the sensor and the sheath, such as via a direct electrical connection, a capacitive or inductive coupling or an optical link. The sheath, and particularly the signal conductors integrated therein, connects to a cable which in turn connects to another device, such as a processing module or computer.

17 Claims, 2 Drawing Sheets

AUXILIARY COMPONENT FOR MEDICAL DEVICE HAVING ADDITIONAL FUNCTIONALITY

BACKGROUND OF THE INVENTION

1. Field of the Invention

This invention relates to the field of medical devices. In one embodiment, this invention relates to the field of filmless dental radiography.

2. Description of the Related Art

In clinical practice, medical devices are very often used in conjunction with an auxiliary component. A common example is a conventional oral thermometer, which when used to take a patient's temperature, is covered with a protective sheath. The thermometer performs the primary function of taking a temperature and the sheath performs the ancillary function of providing a hygienic barrier between the thermometer and the environment within the patient's oral cavity. The auxiliary component in that situation serves only to provide the hygienic barrier, and does not serve other purposes.

Auxiliary components are also used in the field of filmless dental radiography. By way of general background, dentists and oral surgeons typically use x radiation to obtain images of their patient's teeth, mouths and gums to aid in diagnosis and treatment. In traditional oral and dental radiography, a cartridge containing photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth.

In the last several decades, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire development process, including the use of potentially harmful chemicals. In addition, because the images are generated electronically, they can be stored electronically in a computer database.

Because electronic sensors, unlike film, are re-usable from patient to patient, it is common to use a sterile, x-ray permeable sheath that surrounds the sensor. For example, U.S. Pat. No. 6,811,312 depicts a sheath 12 that surrounds a sensor 10 and cable 14. Such sheaths are typically disposable, and are changed between examinations, so that no sheath is used for more than one patient. In this manner, the sheath protects the re-usable sensor from contamination. Protective sheaths, however, have heretofore been used only for the purpose of providing a hygienic barrier, and there has been little or no efforts at utilizing them for any other purposes.

On the other hand, conventional digital dental radiography systems are not without their drawbacks. For example, the connection between the sensor and the processing module or computer is most conventionally made via a cable. Such a cable, however, can be uncomfortable for and annoying to the patient in whose mouth the intraoral sensor is placed. The cable is also bothersome to the dental practitioner when positioning the sensor in the patient's mouth.

In addition, the repeated acts of positioning and re-positioning the cable, which involve a good deal of bending, twisting and pulling of the cable, puts mechanical stresses on the cable. These stresses can eventually lead to cable failure, and indeed cable-related malfunctions are one of most prevalent reasons for product failures and returns in this field.

One class of solution to this problem is to eliminate the cable altogether, and provide an electronic sensor that communicates with a processing module or computer over a wireless link. Such a solution has been set forth, for example, in U.S. Pat. Nos. 7,193,219 and 6,924,486. Such wireless solutions, while excellent for their intended purposes, increase the complexity of the sensor, and impose limitations on the amount of power available to the sensor. Accordingly, such solutions may not always be the most desirable.

Another solution that has been proposed is to utilize a removable cable, which can be attached to and detached from the sensor body by the dental practitioner. Such a solution is described in U.S. Pat. No. 6,030,119. This solution, however, does not solve all of the aforementioned problems. In particular, while this approach may be effective to minimize the mechanical stresses that are put on the cable, and to that extent increases cable life and reduces cable failure rate, it does little to address positioning problems and nothing to address patient comfort problems, since large protrusions are required to receive the detachable cable (see for example projected portions 43 shown in FIGS. 5 and 6 of U.S. Pat. No. 6,030,119). These protrusions hamper positioning efforts as much or nearly as much as the cable itself, and contribute significantly to overall patient discomfort.

The short-comings of the apparatus of U.S. Pat. No. 6,030,119 highlight why a wholly-satisfactory solution to the cable problem has heretofore been so elusive, namely as a result of the requirements of the cable itself. On the one hand, the cable must survive multiple cycles of bending, twisting and pulling during its lifetime, and in that sense it is desirable to make the cable as sturdy as possible. On the other hand, the cable should be flexible, soft, comfortable and utilize a connection junction as small as possible so as to provide simple positioning for the dental practitioner and allow comfortable placement in the patient's oral cavity during an x-ray exam. These requirements, which in a certain sense are at odds with one another, have heretofore prevented a solution which addresses all of the problems presented by the cable, including the positioning problems, comfortable problems and failure problems, without detracting from the overall performance of the system.

Accordingly, the problems presented by the cable in a wired digital dental radiography system have not been adequately solved. At the same time, the auxiliary component with which the electronic sensor is conventionally used, namely the sheath, has heretofore only served to provide a hygienic barrier between the sensor and the patient's oral cavity, and its presence and availability has yet to be exploited for any other purpose.

SUMMARY OF THE INVENTION

It is an object of the present invention to provide an auxiliary component that is conventionally used for one purpose, with additional functionality, so that the auxiliary component may be utilized for an additional purpose or purposes.

It is another object of the present invention to provide additional functionality to an auxiliary component, that enables the auxiliary component to solve a problem of the medical device.

It is another object of the present invention to provide an electronic dental sensor that exhibits improved positioning capability.

It is another object of the present invention to provide an electronic sensor that is more comfortable to the patient.

It is another object of the present invention to provide an electronic sensor that exhibits a reduced cable failure rate.

DETAILED DESCRIPTION OF PREFERRED EMBODIMENTS

In one embodiment, the present invention equips a protective sheath that is conventionally used to provide a hygienic barrier between an electronic intraoral sensor and a patient's oral cavity, with conductive capability such that the sheath may additionally function as a conduit for signal and power transfer to and from the sensor. More specifically, in such an embodiment the present invention provides a sheath with integrated conductive traces, so that the sheath serves as an intermediate electrical connection between the electronic sensor and a cable. The sheath may be disposable. The sensor communicates with conductors integrated into the sheath, and the conductors in turn communicate with the cable.

The cable may be connected directly to a computer or to an interface board in a computer, or may be connected to an intermediate processing module. In the latter case, communication between the processing module and computer may be over a bi-directional wired or wireless link. The computer, interface board and/or processing module may perform control and processing functions, which may include, among other things, controlling the operation of the sensor, reading out data from the sensor, effecting analog-to-digital conversion, executing an event detection algorithm and processing data read-out of the sensor into a form suitable for transmission, such as for example transmission from the processing module to the computer.

In clinical practice, a sheath is typically disposable and used for only one or a few examinations. Thus, a marked advantage of the present invention is that the sheath and its conductive traces will be subject to most of the mechanical stresses to which the cable would be subject in a conventional system, but because the sheath is disposable, it need not meet the rigorous survival requirements of a conventional cable. The cable in the present invention, on the other hand, is not subjected to the same mechanical stresses as a cable in a conventional system, and will therefore exhibit a much lower failure rate and a much longer life span.

Figure 1:
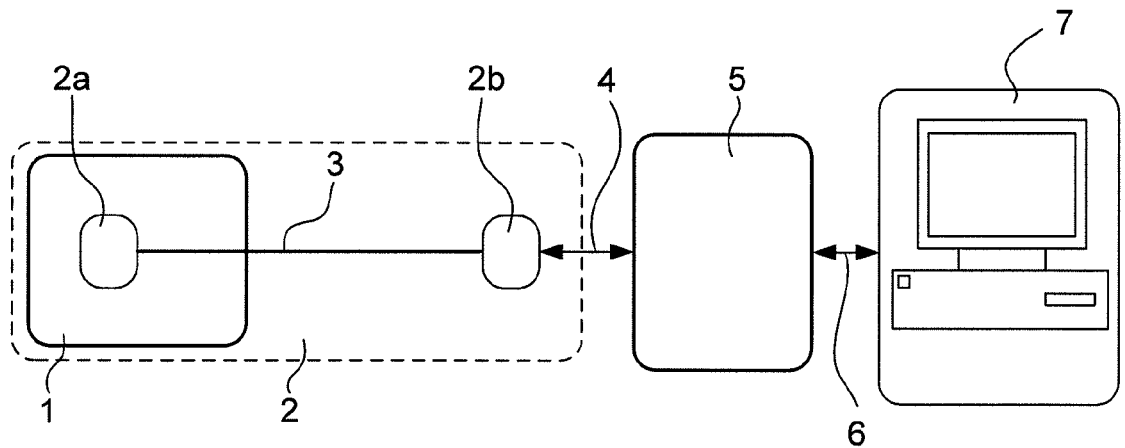
FIG. 1 is a block diagram of a first embodiment of the present invention.

A block diagram of an embodiment of the present invention is shown in FIG. 1. Sensor 1 is surrounded by sheath 2. The sheath may be made of a variety of materials. Some examples include plastic films (such as polyethylene, cellulose, vinyl, PVC and the like), thermoplastic elastomers, silicones, rubbers and synthetic paper (such as Tyvek® and the like). Other synthetic or non-synthetic materials may be used as well.

Integrated in the sheath 2 are miniature electrical connectors 2a and 2b and a conductive trace 3 between the connectors 2a and 2b. Such components may be integrated in the sheath 2 by a variety of methods, such as for example by a lamination process. Other methodologies which may be used include a direct deposition/printing process, a bonding/secondary assembly process and a process in which the components to be integrated are molded-in. Other alternatives exist as well.

Miniature connector 2a connects to the sensor 1 via a connection point provided on the sensor 1. Miniature connector 2b connects to the cable 4 and conductive trace 3 provides for communication between the two miniature connectors. Electrical signals are conveyed to and from the electronic sensor 1 via the conductive trace 3. The electrical signals may be for example electronic information signals and/or electrical power.

In one embodiment of the present invention, a band, such as an elastic band, may be provided around the sheath in the vicinity of the connector 2a to ensure a proper connection between the connector 2a and the connection point on the sensor 1. Cable 4 connects on its other end to processing module 5, which in turn connects to computer 7 via link 6. Link 6 may be wired or wireless, and should provide for bi-directional communication between processing module 5 and computer 7.

Figure 2:
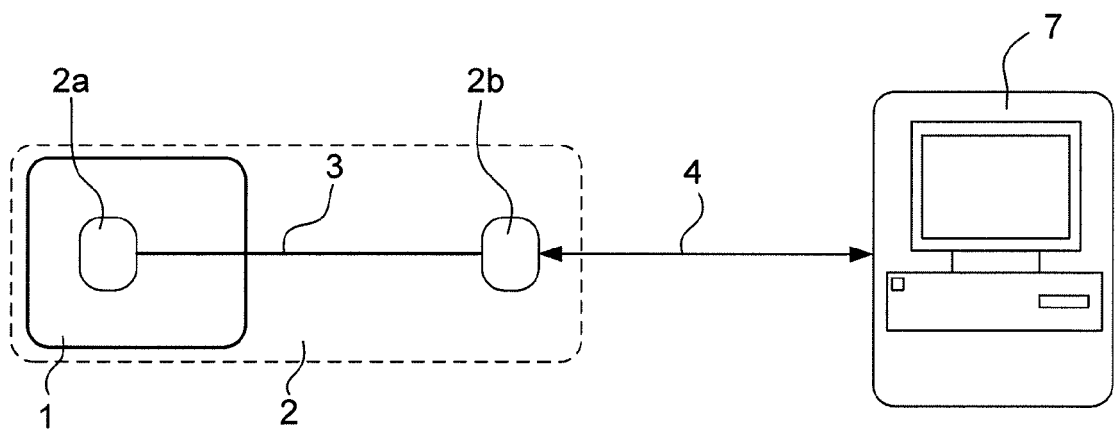
FIG. 2 is a block diagram of a second alternative embodiment of the present invention.

FIG. 2 depicts an alternate embodiment of the present invention, in which cable 4 connects directly to computer 7, rather than via a processing module and additional link. In this alternative embodiment, a specialized interface board may be housed in computer 7, which interface board may receive signals from the cable in the first instance. In either the embodiment of FIG. 1 or 2, the connection to the computer may be via the PCI slot, the ISA slot or the USB port.

In one preferred embodiment of the present invention, trace 3 comprises multiple traces, such as for example conductive trace 3a for conveying electronic information signals such as image data signals and control signals, and conductive trace 3b for conveying electrical power. This configuration is depicted schematically in FIG. 3.

Figure 3:
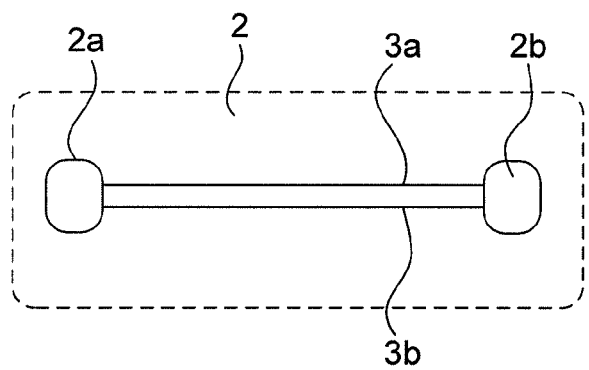
FIG. 3 illustrates a sheath in accordance with an embodiment of the present invention, having a pair of conductive traces integrated therein.
Figure 4:
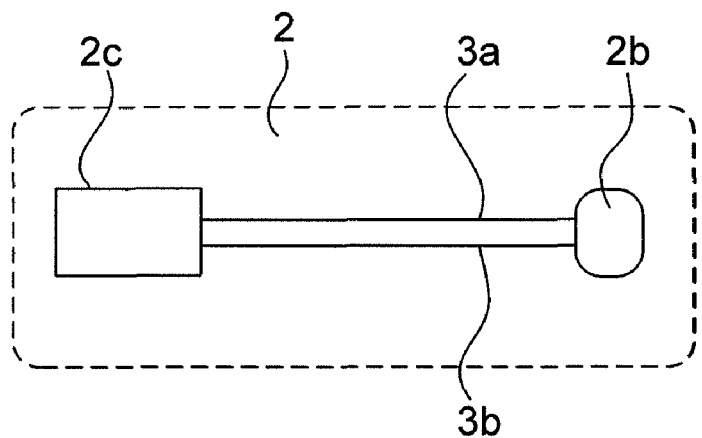
FIG. 4 illustrates a sheath in accordance with another embodiment of the present invention.
Figure 5:
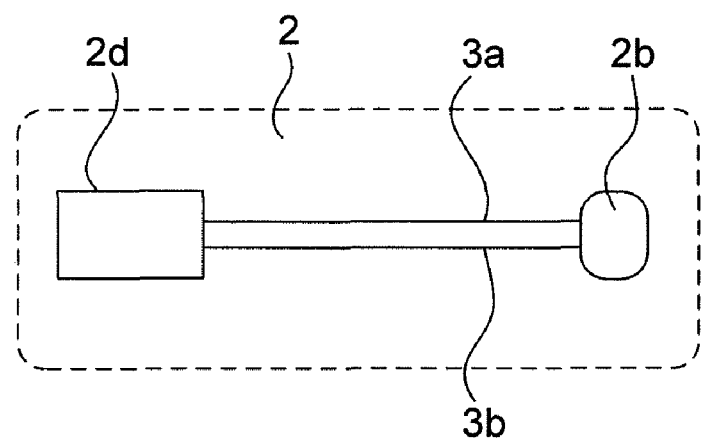
FIG. 5 illustrates a sheath in accordance with yet another embodiment of the present invention.

Alternatives to the configurations of FIGS. 1, 2 and 3 are also possible. For example, as shown in FIG. 4 connector 2a might be replaced with a near field transceiver 2c integrated into the sheath 2, which can communicate with sensor 1 via near field coupling, such as capacitive coupling, inductive coupling and the like. As shown in FIG. 5, connector 2a might also be replaced with an optical transceiver 2d integrated into the sheath 2, which can communicate with the sensor via an optical link. Combinations of the foregoing are also possible. For example, both a near field transceiver and a miniature electrical connector (or an optical transceiver and a miniature electrical connector) may be integrated into the sheath in lieu of miniature electrical connector 2a alone, such that data and control signals are communicated to and from the sensor via the near field transceiver (or optical transceiver) and power is communicated to the sensor via the miniature electrical connector. Other variations are possible as well. In each of the foregoing variations, the sensor 1 is configured with near field transceiver or optical transceiver as well, which communicates with the corresponding transceiver that is integrated in the sheath 2.

The foregoing provides several concrete examples of how an auxiliary component that is commonly used with a medical device may be modified to provide it with additional functionality. As a result of such modifications, the auxiliary component is made to perform an additional function, wholly different from its conventional function, and thereby solve a problem that has plagued the device itself. The present invention is not limited in its applicability to the specific case of modifying a hygienic sheath to enable it to provide electrical communication, but to the contrary is applicable to any case in which an auxiliary component may be modified to provide additional or enhanced functionality.

Moreover, it is understood that the above description and drawings are illustrative of the present invention and details contained therein are not to be construed as limitations on the present invention. Changes in components, procedure and structure may be made without departing from the scope of the present invention as defined in the following claims.

What is claimed is:

1. An intraoral imaging system comprising:
    an electronic sensor; and
    a sheath that surrounds the electronic sensor, the sheath having at least one conductive trace integrated therein that provides an electrical communication path to and from the electronic sensor.

2. An intraoral imaging system according to claim 1, further comprising a cable.

3. An intraoral imaging system according to claim 2, wherein the sheath further has integrated therein a first electrical connector that connects to the electronic sensor and a second electrical connector that connects to the cable, the first and second electrical connectors being disposed on opposite sides of the conductive trace.

4. An intraoral imaging system according to claim 1, wherein the sheath has integrated therein at least two conductive traces that provide at least two conductive paths to and from the electronic sensor, including a first conductive path that conveys electronic information signals and a second conductive path that conveys electrical power.

5. An intraoral imaging system according to claim 4, wherein the electronic information signals comprise image data signals and control signals.

6. An intraoral imaging system according to claim 1, wherein the sheath further has integrated therein a near field transceiver that provides for communication between the sensor and the conductive trace.

7. An intraoral sensor according to claim 6, wherein the near field transceiver communicates with the sensor via capacitive coupling.

8. An intraoral sensor according to claim 6, wherein the near field transceiver communicates with the sensor via inductive coupling.

9. An intraoral imaging system according to claim 1, wherein the sheath has further integrated therein an optical transceiver that provides for communication between the sensor and the conductive trace.

10. A method of providing electrical communication to and from an electronic sensor, comprising the steps of:
    surrounding the electronic sensor with a sheath having at least one conductive trace integrated therein; and
    conveying electrical signals to and from the electronic sensor via said conductive trace.

11. The method according to claim 10, wherein the electrical signals conveyed to and from the sensor comprise electronic information signals and electrical power.

12. The method according to claim 11, wherein the electronic information signals and electrical power are conveyed via the conductive trace between the electronic sensor and a cable.

13. The method according to claim 11, wherein the electronic information signals are conveyed to and from the electronic sensor via a first conductive trace integrated in the sheath and the electrical power is conveyed to and from the electronic sensor via a second conductive trace integrated in the sheath.

14. A medical diagnostic system comprising:
    a primary component configured to perform a main function; and
    an auxiliary component configured to perform a first ancillary function and further configured to perform a second ancillary function separate and distinct from the first ancillary function, wherein
    the primary component is an electronic component, the first ancillary function is to provide a hygienic barrier around a main component and the second ancillary function is an electrical function.

15. A medical diagnostic system comprising:
    a primary component configured to perform a main function; and
    an auxiliary component configured to perform a first ancillary function and further configured to perform a second ancillary function separate and distinct from the first ancillary function, wherein
    the primary component is an electronic component, the first ancillary function is a mechanical function and the second ancillary function is an electrical function,
    the auxiliary component includes a mechanical sub-component that performs the first ancillary function and an electrical sub-component integrated in the mechanical sub-component that performs the second ancillary function, and
    the mechanical sub-component comprises a sheath and the electrical sub-component comprises at least one conductive trace.

16. The medical diagnostic according to claim 15, wherein the first ancillary function is to provide a hygienic barrier around the main component.

17. The medical diagnostic according to claim 15, wherein the second ancillary function is to convey electrical signals to and from the main component.

* * * * *